United States Patent
Svagelj et al.

(10) Patent No.: US 9,938,554 B2
(45) Date of Patent: Apr. 10, 2018

(54) CO-CULTIVATION OF PROPIONIBACTERIUM AND YEAST

(71) Applicants: Acies Bio d.o.o., Ljubljana (SI); Arima d.o.o., Ljubljana (SI)

(72) Inventors: Mirjan Svagelj, Ljubljana (SI); Stefan Fujs, Ljubljana (SI); Gregor Kosec, Ljubljana (SI); Hrvoje Petkovic, Ljubljana (SI)

(73) Assignees: Acies Bio d.o.o., Ljubljana (SI); Arima d.o.o, Ljubljana (SI)

( * ) Notice: Subject to any disclaimer, the term of this patent is extended or adjusted under 35 U.S.C. 154(b) by 0 days.

(21) Appl. No.: 15/309,869

(22) PCT Filed: May 8, 2015

(86) PCT No.: PCT/EP2015/060270
§ 371 (c)(1),
(2) Date: Nov. 9, 2016

(87) PCT Pub. No.: WO2015/169967
PCT Pub. Date: Nov. 12, 2015

(65) Prior Publication Data
US 2017/0145467 A1  May 25, 2017

(30) Foreign Application Priority Data

May 9, 2014 (EP) .................................. 14167774

(51) Int. Cl.
*C12P 19/42* (2006.01)
*C12P 39/00* (2006.01)
*C12N 1/16* (2006.01)

(52) U.S. Cl.
CPC ............... *C12P 39/00* (2013.01); *C12N 1/16* (2013.01); *C12P 19/42* (2013.01)

(58) Field of Classification Search
CPC .................................. C12N 1/16; C12P 39/00
See application file for complete search history.

(56) References Cited

U.S. PATENT DOCUMENTS 5,260,061 A  11/1993  Ayres et al.

FOREIGN PATENT DOCUMENTS

| CN | 101045910 A | 10/2007 |
| WO | 2008/030089 A1 | 3/2008 |
| WO | 2011/140649 A1 | 11/2011 |

OTHER PUBLICATIONS

International Search Report and Written Opinion of the International Search Authority for corresponding International Application No. PCT/EP2015/060270 dated Sep. 14, 2015.
International Preliminary Report on Patentability for corresponding International Application No. PCT/EP2015/060270 dated Jun. 1, 2016.

(Continued)

*Primary Examiner* — Kara Johnson
(74) *Attorney, Agent, or Firm* — Renner, Otto, Boisselle & Sklar, LLP

(57) ABSTRACT

The invention provides a fungal cell, such as a yeast cell, capable of growing in co-cultivation with *Propionibacterium*. Also provided are methods of producing such cells and fermentation processes using the fungal cell of the invention and *Propionibacterium* in co-cultivation. Such co-cultivation significantly reduces the chemical oxygen demand load of the waste fermentation broth.

12 Claims, 3 Drawing Sheets

(56) References Cited

OTHER PUBLICATIONS

Danilova et al., "A Positive Effect of Propionibacterium freudenreichii on the Growth of *Saccharomyces cerevisiae* during Their Cocultivation", Applied Biochemistry and Microbiology, vol. 42, No. 4, Jul. 1, 2006, pp. 378-383.
Athanasiadis et al., "Whey Liquid Waste of the Dairy Industry as Raw Material for Potable Alcohol Production by Kefir Granules", Journal of Agricultural and Food Chemistry, vol. 50, No. 25, Dec. 1, 2002, pp. 7231-7234.
Miyano et al., "Improvement of vitamin B12 fermentation by reducing the inhibitory metabolites by cell recycle system and a mixed culture", Biochemical Engineering Journal 6, 2000, pp. 207-214.
Stratford et al., "Extreme resistance to weak-acid preservatives in the spoilage yeast Zygosaccharomyces bailii", International Journal of Food Microbiology, vol. 166, No. 1, Aug. 1, 2013, pp. 126.134.
Mira et al., "Adaptive Response and tolerance to Weak Acids in *Saccharomyces cerevisiae*: A Genome-Wide View", OMICS: A Journal of Integrative Biology, vol. 14, No. 5, Oct. 1, 2010, pp. 525-540.
Communication pursuant to Article 94(3) EPC issued in corresponding European Patent Application No. 15 723 471.7 dated Apr. 3, 2017.
Grum-Grzhimaylo et al., "On the diversity of fungi from soda soils", Fungal Diversity, vol. 76, 2016, pp. 27-74.

US 9,938,554 B2

CO-CULTIVATION OF PROPIONIBACTERIUM AND YEAST

This application is a national phase of International Application No. PCT/EP2015/060270 filed May 8, 2015 and published in the English language, which claims priority to Application No. EP 14167774.0 filed May 9, 2014.

FIELD OF THE INVENTION

The present invention is in the field of bioprocess technology, in particular, of bioprocesses using co-cultures of yeast and propionibacterium (i.e., *Propionibacterium* sp.).

BACKGROUND OF THE INVENTION

Waste streams with a high organic chemical oxygen demand (COD) are an ecological burden that has to be dealt with accordingly. These waste streams can be by-products of different industries such as dairy, fruit and vegetable or sugar processing industries. An example is whey that is produced by the dairy industry as a by-product resulting from cheese making. This process results in high volumes of whey (sweet or sour) that have a high COD but on the other hand cannot be easily/economically utilised otherwise, due to the low relatively low content of useful dry content, e.g. milk protein and lactose.

Depending on the process of cheese manufacture the COD value of leftover whey can range from 35,000 mg $O_2$/L to 100,000 mg $O_2$/L. The main contributor of the high organic load is lactose, which can represent up to 90% of the COD value. In the case of sour whey the presence of lactic acid even increases this problem. Lactose also represents about 75% of the whey dry matter and as such can be exploited by processes utilizing microorganisms. Several solutions of whey utilisation have been studied, such as bioethanol and biogas production, extraction of lactose or proteins, production of organic acids or biomass, but there is still a need of an economical way of whey utilisation.

WO 2011/140649 describes the utilization of whey by a mixed culture of lactic acid bacteria and yeast for the production of edible biomass. The process can successfully decrease the COD load of whey, but the final product has little commercial value.

Whey can be used for the cultivation of bacteria from the genus *Propionibacterium* sp., belonging to the order of Actinomycetales (Bergey's Manual of Systematic Bacteriology (1st Edition, 1986)). *Propionibacterium* sp. are known producers of valuable products such as organic acids (propionic and acetic acid), vitamin B12 and bifidogenic compounds. While *Propionibacterium* sp. can be successfully cultivated on whey they cannot lower the COD load satisfactorily as they produce organic acids which accumulate in the fermented (spent) whey and contribute significantly toward the final COD load. In the following, the terms "*Propionibacterium* sp." and "*propionibacterium*" are used interchangably.

Co-cultures of *Propionibacterium* sp. and other bacteria are known to be able to decrease the COD load of the spent medium (Miyano et al., 2000), but such processes have the disadvantage of not being food grade and as such being exempt from being used inside food processing plants.

The metabolites produced by *Propionibacterium* sp. are known to inhibit the growth of other microorganisms, especially fungi, and their use in food-spoilage prevention is well known. U.S. Pat. No. 5,260,061 describes the application of *Propionibacterium* sp. metabolites for food applications to inhibit the growth of yeast. WO 2008/030089 describes co-cultivation of *Propionibacterium* sp. with yeast for the purpose of obtaining good flavour/aroma characteristics in the cheese making process. In this case, *Propionibacterium* sp. was used to control and finally inhibit the growth of yeast in the mixed culture as the yeast cell applied was not tolerant to growth-inhibiting substances from *Propionibacterium* sp.

In view of the above stated prior art, it is an object of the invention to provide novel bioprocesses for producing valuable biotechnological products from sweet or sour whey where the final spent fermentation media exhibit a relatively low COD. Another object of the invention is to provide fungal cells useful in processes of the invention.

SUMMARY OF THE INVENTION

The present invention meets the objectives stated above by providing novel fungal cells, preferably yeast cells, which are capable of growing in co-cultivation with *propionibacterium*. Such fungal cells or cells may be characterized/defined by their ability to grow on stationary-phase supernatant (spent medium) resulted after *propionibacterium* cultivation. The present invention also relates to biotechnological processes using such fungal cells which can grow in the presence of said medium in co-culture with *propionibacterium*.

Hence, a first aspect of the present invention relates to fungal cell capable of growing in a stationary-phase supernatant of a *propionibacterium* cultivation.

Such a fungal cell can reproducibly be obtained by mutagenesis/selection procedures described in this patent application. Fungal cells, in particular yeast cells, having the capability of growing in a stationary-phase supernatant of a *propionibacterium* cultivation are useful for the reduction of the COD load of waste materials from fermentation processes according to the invention. Such fungal cells (in particular such yeast cells) were heretofore not available to the person skilled in the art.

Fungal cells of the invention can easily be identified and distinguished from other fungal cells by procedures disclosed herein below. In particular, a well-defined cultivation medium and well defined cultivation conditions of *propionibacterium* therein are disclosed for testing the capability of a fungal cell of "growing in a stationary-phase supernatant of a *propionibacterium* cultivation", according to the invention.

Hence, in a preferred embodiment, the stationary-phase supernatant, (to be used for testing whether the fungal cell is one according to the invention) is obtained from a stationary culture of *Propionibacterium freudenreichii* cultivated under anaerobic conditions at 35° C. and pH 6.5 in a medium consisting of 60 g/L sweet whey powder, 5 g/L yeast extract, and 40 mg/L calcium D-pantothenate. Preferably, the sweet whey powder has food-grade quality, and preferably it contains at least 63% wt. lactose, at least 10% wt. protein and at most 5% wt. water.

The capability of growing in a stationary-phase supernatant of a *propionibacterium* cultivation, the cultivation of fungal (yeast) culture can be defined in terms of the maximum growth rate achieved by the fungal cell when growing in a stationary-phase supernatant of a *propionibacterium* cultivation. Hence, in another preferred embodiment, said capability of growing of said fungal cell in a stationary-phase supernatant of a *propionibacterium* cultivation is defined as the capability of said fungal cell of growing on said stationary-phase supernatant at a maximum growth rate ($\mu_{max}$) of at least 0.02 h$^{-1}$. Methods of determining the growth rate of a microorganism in culture are well known in the art.

The stationary culture state of a *propionibacterium* culture may be indicated by a constant concentration of acetic acid and propionic acid in the culture medium over time when the culture is not exposed to aeration. In another embodiment, the stationary state of the *propionibacterium* culture is indicated by a constant cell density of *propionibacterium* (in g(DW)/L) over time.

In a preferred embodiment, the ability of the fungal cell to grow in a stationary-phase supernatant of a *propionibacterium* cultivation is tested in the test method described in Example 2, herein below.

The preferred fungal cell is a yeast cell.

In one embodiment, the yeast cell is the yeast cell deposited on Jan. 14, 2014 at Deutsche Sammlung von Mikroorganismen und Zellkulturen (DSMZ) under accession number DSM 28271.

A second aspect of the invention relates to a process for producing a biotechnological product, said process comprising co-cultivation of *propionibacterium* and a fungal cell in a cultivation medium. The fungal cell is preferably capable of growing in a stationary-phase supernatant of a *propionibacterium* cultivation.

The fungal cell is preferably a yeast cell, such as a fungal cell according to the invention, as described hereinabove and below.

The biotechnological product is preferably one which is produced by *propionibacterium*.

A preferred biotechnological product is vitamin B12.

In a preferred embodiment, the process includes a first phase with no aeration followed by a second phase in which aeration occurs. Preferably, both the phases are at least 24 hours, or 48 hours, or 72 hours long.

In a preferred embodiment, at least 90% of the growth of the *propionibacterium* [in % gram dry weight] occurs during said first phase without aeration.

In another preferred embodiment, at least 90% of the growth of the fungal cell [in % gram dry weight] occurs during said second phase in which aeration occurs.

In another preferred embodiment, the chemical oxygen demand (COD) of the cultivation medium is reduced to a level of equal to or less than 25%, preferably equal to or less than 10%, or equal to or less than 1%, of the initial COD of the cultivation medium.

In another preferred embodiment, the cultivation medium is (or comprises) whey. The cultivation medium is or comprises, e.g., sweet whey, or sour whey.

Preferably, in processes of the invention, said fungal cell is added at or after the point in time when said *propionibacterium* has reached at least 90% of its maximum cell density [g(DW)/L] in the culture. In other embodiments of the process of the invention, the fungal cell is added when or after the *propionibacterium* has reached its stationary growth phase.

The invention further relates to a method of making a *propionibacterium*-tolerant fungal strain, such as a *propionibacterium*-tolerant yeast strain. The method comprises:
1. Obtaining a starting fungal strain.
2. Exposing the starting fungal strain to a mutagenic agent and/or to a mutagenic condition.
3. Cultivating the exposed fungal strain of step 2 in the presence of first concentrations of acetic acid and/or (preferably "and") propionic acid.
4. Optionally exposing said cultivated fungal strain of step 3 to a mutagenic agent and/or to a mutagenic condition and cultivating said optionally exposed fungal strain in the presence second concentrations of acetic acid and/or (preferably "and") propionic acid, wherein said second concentrations are preferably higher than said first concentrations, respectively.
5. Exposing the cultivated fungal strain of step 3 or 4 to a mutagenic agent and/or to a mutagenic condition.
6. Cultivating the exposed fungal strain of step 6 in a medium comprising stationary-phase supernatant of a *propionibacterium* cultivation.
7. Optionally repeating step 7 with increasing concentrations of the stationary-phase supernatant of a *propionibacterium* cultivation.
8. Thereby obtaining a fungal cell capable of growing in a stationary-phase supernatant of a *propionibacterium* cultivation.

A preferred mutagenic agent in accordance with the invention is ethyl methanesulfonate. Any other mutagenic agent, i.e. chemical or physical can however be used which increases the frequency of mutation occurrence. Known mutagenic agents which can be used in the above method include: Reactive oxygen species (ROS), such as superoxide, hydroxyl radicals and hydrogen peroxide; deaminating agents, for example nitrous acid; polycyclic aromatic hydrocarbon (PAH); alkylating agents such as ethylnitrosourea or methyl methanesulfonate; guanine; nitrosamines; nitrosoguanidine; mustard gas; vinyl chloride; aromatic amines; amides; 2-acetylaminofluorene; alkaloid from plants; such as those from *Vinca* species; bromine; compounds that contain bromine in their chemical structure; sodium azide; benzene. Suitable mutagenic conditions or physical mutagens are, e.g., UV irradiation, exposure to X-ray, and/or exposure to radioactivity.

The skilled person will appreciate that steps 2 to 4 above can be omitted, e.g., if the starting strain in step 1 is already sufficiently tolerant to acetic acid and/or propionic acid, or otherwise able to grow in a medium comprising stationary-phase supernatant of a *propionibacterium* cultivation. In this case the starting strain from step 1 is directly exposed to the mutagenic agent and/or condition in step 5.

A further aspect of the present invention relates to a fungal strain obtained by the above method.

DETAILED DESCRIPTION OF THE INVENTION

Figure 1:
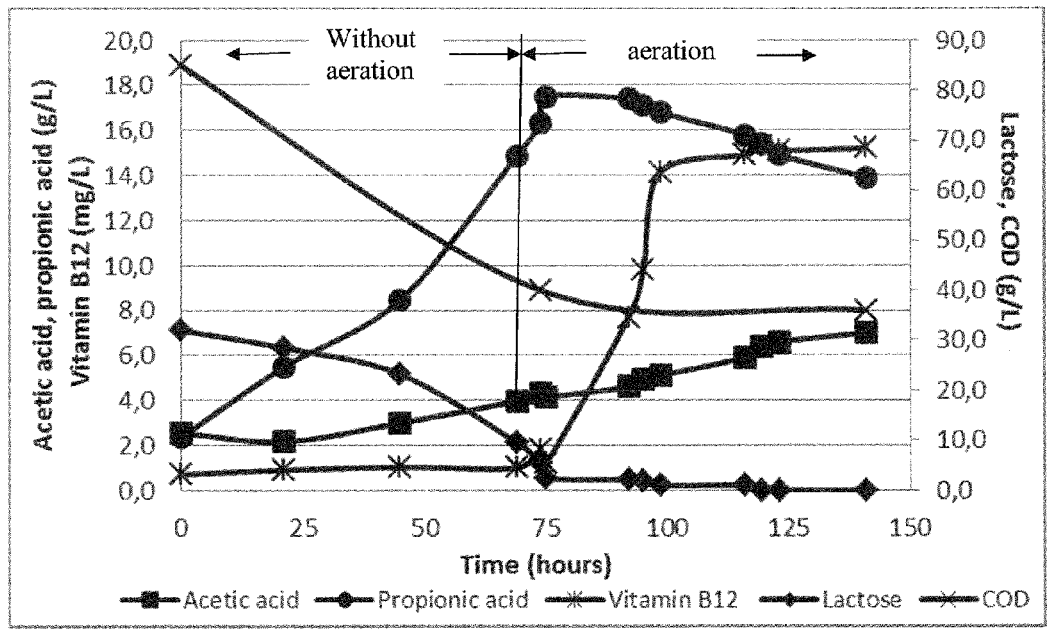
FIG. 1 shows the utilization of lactose by *Propionibacterium* sp. and the production of acetic and propionic acid and vitamin B12 in a two stage process on whey. In this way the COD value can be reduced from 85000 mg O$_2$/L to 36000 mg O$_2$/L. Up to 75 hours the fermentation was carried out without aeration and after 75 hours aeration was introduced.
Figure 2:
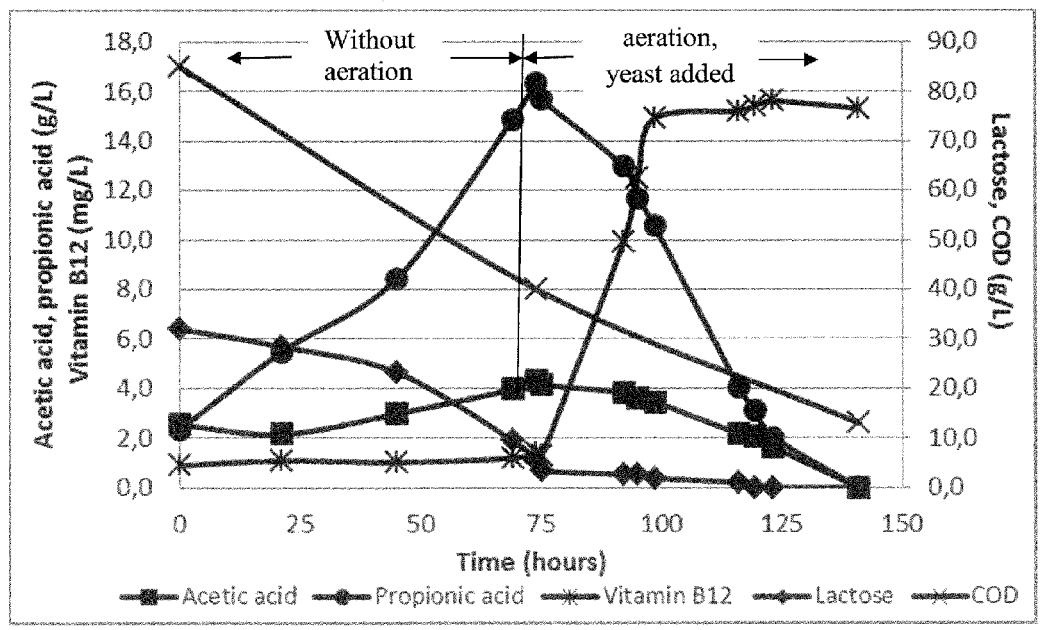
FIG. 2 shows the utilization of lactose by *Propionibacterium* sp. and the production of acetic and propionic acid and vitamin B12 in a two stage process on whey where tolerant DSM 28271 yeast culture was added in the stage where oxygen was introduced. In this way the COD value can be reduced from 85000 mg O$_2$/L to 13000 mg O$_2$/L. Up to 75 hours the fermentation was carried out without aeration and after 75 hours yeast and aeration was introduced.

The expression "supernatant", or "culture supernatant", in the context of the present invention, means the liquid obtained when filtrating or centrifuging a fermentation broth, thus removing cells and other insoluble material. The supernatant contains any nutrients and other components of the culture medium not (yet) consumed by the microorganism or degradation products, and any products produced by the microorganism during fermentation.

"Culture medium" shall be understood as being a nutrient-containing medium in which a microorganism can grow. Liquid culture media are preferred.

"Broth" or "fermentation broth" shall be understood as referring to a culture medium in which a microorganism grows, or has grown. A broth may comprise non-used nutrients and/or products produced by the microorganism.

A "stationary-phase supernatant" or "spent medium", in accordance with the present invention shall be understood as being a supernatant from a stationary-phase fermentation broth.

The stationary phase shall be understood the phase of the cultivation in which the microorganism has substantially ceased to grow, e.g., the microorganism has reached its maximum cell density during the cultivation. The stationary phase of a cultivation can also be detected by monitoring the concentration of fermentation products. In one embodiment the stationary phase of a *propionibacterium* cultivation is defined as the phase starting from the point in time at which the concentration of acetic acid and/or propionic acid have reached its maximum value, or alternatively have reached 90% of its maximum value.

"Whey" is a by-product in the dairy industry, which separates from milk after curdling, when rennet or an acidic substance is added or formed in situ. "Sweet whey" is manufactured during the making of rennet types of hard cheese like cheddar or Swiss cheese. "Acid whey", or "sour whey" is a by-product produced during the making of acid types of dairy products such as cottage cheese or strained yogurt.

The "chemical oxygen demand" or "COD" shall be understood as being the chemical oxygen demand as determined by ISO 6060:1989 standard method. It is understood that a sample may have to be diluted with water, if the COD to be determined is above the allowed maximum COD of 700 mg/L, according to this method. The COD is then calculated from the determined COD by multiplication with the dilution factor.

The present invention provides fungal cells, tolerant to co-cultivation with *propionibacterium*. This invention also provides a process of co-cultivating *propionibacterium* and a fungal cell, which cell is tolerant to inhibitory compounds produced by *propionibacterium*.

The invention provides fungal cells, which are capable of growing in the presence of *propionibacterium* and their inhibitory metabolites. These cells are obtained by procedures of selection of naturally occurring random mutants of generally available fungal cells on growth substrates in which *propionibacterium* has been previously cultivated. Preferably, selection of such tolerant fungal cells is carried out in at least two steps. In the first step random mutants of fungal cells are selected that can tolerate higher concentrations of organic acids, for example acetic acid and propionic acid. In the second step, random mutants of these acid-tolerant cells are subjected to additional round of selection on used growth medium in which *propionibacterium* has been previously cultivated and reached stationary phase of growth. Preferably the fungal cells, provided by this invention are yeast cells.

The fungal cells of this invention, which are tolerant to co-cultivation with *propionibacterium*, e.g., capable of growing in a stationary-phase supernatant of a *propionibacterium* culture, can be obtained by classical selection methods, possibly supported by random mutagenesis, by genetic engineering or by screening natural isolates.

A biotechnological process of the invention using tolerant yeast cells in a process of co-cultivation with *propionibacterium* may include the following steps:
1. Preparation of the culture medium
2. Inoculation with *propionibacterium*.
3. Fermentation without aeration
4. Switching to aerobic conditions
5. Inoculation with a tolerant yeast cell
6. Continuation of the fermentation as a co-cultivation of *propionibacterium* and yeast
7. Optionally downstream processing and product recovery The Fermentation Medium The fermentation medium can be any suitable fermentation medium in which both *propionibacterium* and fungal cells can grow. For example the fermentation medium may comprise molasses or whey. The fermentation medium may be composed of waste streams from different industries (such as whey) to which specific additives (such as minerals, vitamins, nitrogen and additional carbon sources, precursors etc.) may be added to increase the growth rate or the formation of desired products. The medium can contain different carbon sources such as glucose, lactose, fructose, lactic acid and nitrogen sources such as ammonium sulphate, amino acids, peptides and proteins that are suitable for *propionibacterium*. The pH value of the fermentation medium may be adjusted at the beginning of the process or can be maintained during the fermentation process to allow good growth of *propionibacterium* and/or product formation.

The medium is normally treated by a process to inactivate a sufficient proportion of microorganisms that would be initially present in the fermentation medium, before the inoculation with *propionibacterium*. These processes can be sterilization/pasteurization, e.g., autoclaving, filtration, irradiation and/or chemical treatments.

The cultivation vessel or fermenter should be prepared by a method that enables the removal of a sufficient proportion of microorganisms initially present and then filled with the fermentation medium. The cultivation vessel to be used in processes of the invention can be very simple, as long as it can maintain a desired temperature, and can maintain adequate stirring to prevent large pH or nutrient gradients. It can ideally withhold slight overpressure.

Inoculation with *Propionibacterium*

The inoculum with *propionibacterium* can consist of one or several stages depending on the final seed culture volume and the process used. The inoculum may be prepared in a medium that supports the growth of *propionibacterium*. The inoculum is cultivated at the preferred temperature for the desired time after which it can be used to inoculate the fermentation medium. The inoculation volumes for subsequent stages of the inoculum or the fermentation stage can range from 1 to 20%.

Fermentation Without Aeration

The fermentation broth is first maintained without aeration at the desired temperature for optimal growth or product formation. The temperature can be in the range of 25° C. to 40° C., preferably at 35° C. If sugars are present in the fermentation medium the pH value should be maintained at the desired level, which can range from 5.5 to 8.0, preferably at 6.5. The pH can be maintained by several different acids/bases such as $H_2SO_4$, HCl, NaOH, $NH_4OH$, etc. The bioprocess can be carried out without aeration or can be maintained under $CO_2$ and/or $N_2$ sparging and/or overpressure. Cultivation under $CO_2$ overpressure is favoured.

Stirring of the fermentation medium should be sufficient to prevent large pH gradients and can be performed but not limited by Rushton turbines, marine propellers or an internal and/or external recirculation pump.

Switch to Aerobic Conditions

After the nutrients consumable by *propionibacterium* are exhausted the culture can be switched to aerobic conditions. The air can be introduced into the cultivation vessel and should be sufficient for the growth of yeast described below. The aeration rate also influences the rate that yeast metabolises organic acids produced by *propionibacterium*.

Additional supplements may be introduced at this time that either influence the properties of the broth (i.e. antifoam), influence the formation of products produced by *propionibacterium* (i.e. 5,6-dimethylbenzimidazole) or influence the growth or product formation of yeast (nitrogen sources, precursors etc.).

After the culture has been switched to aerobic conditions the pH should again be maintained at the desired level. The pH value can range from 5.5 to 8, preferably at 6.5 to enable good growth of yeast.

Inoculation of the *Propionibacterium*-Tolerant Yeast Cell

The inoculum of the tolerant yeast cell can consist of one or several stages depending on the final volume of the seed culture. The yeast inoculum is prepared in a medium that supports the growth of yeast. The inoculum is cultivated at the preferred temperature for the desired time. The yeast inoculum can then be used to inoculate the fermentation medium with cultivated *propionibacterium* after it has been switched to aerobic conditions. The inoculation volumes for subsequent stages of the inoculum or the final stage can range but are not limited to 1 to 20%. Preferably the yeast inoculum represents 5% of the final volume.

Continuation of the Fermentation by the Resulting Co-Culture of Microorganisms

The fermentation broth is maintained at the desired temperature and the pH value is constantly maintained at the desired level by the addition of the appropriate acid or base. Stirring and aeration should be maintained at required levels to ensure complete utilization of organic acids. The amount of aeration and/or mixing influences the metabolism of organic acids by yeast.

Additional supplements can also be introduced at this time that either influence the properties of the broth (i.e. antifoam), influence the formation of products produced by *propionibacterium* or influence the growth or product formation of yeast. The COD value of the supernatant of the fermentation broth and yield of a valuable product, produced by either *propionibacterium* or yeast cells are monitored to achieve desired properties of the broth. Using such co-cultivation procedure the COD value of the supernatant of the broth can be decreased to less than 20000 mg $O_2/L$, preferably to less than 15000 mg $O_2/L$, more preferably to less than 10000 mg $O_2/L$ and even more preferably to less than 5000 mg $O_2/L$. If the selected high-value product is vitamin B12, the yield of vitamin B12 can be more than 5 mg/L, preferably more than 10 mg/L, more preferably more than 20 mg/L and even more preferably more than 100 mg/L.

Downstream Processing of the Fermentation Broth

After the organic acids are consumed and COD of the supernatant reaches a satisfactory level, the bioprocess is stopped. Mixed *propionibacterium*/yeast biomass together with insoluble components of the broth can be separated from the supernatant by centrifugation, filtration or any other suitable method. The supernatant has low COD and presents a small burden if disposed to the water treatment plant or, in an ideal case, the COD is low enough that it can be disposed directly into the environment. If the biomass is enriched with valuable substances, such as vitamins and proteins, particularly vitamin $B_{12}$, these substances can be used as an additive to animal feed. Alternatively, the biomass can be used as a starting material for isolation of valuable substances, such as vitamin $B_{12}$ in any form (e.g. cyanocobalamin or methylcobalamin). Depending on the grade of purity, vitamin $B_{12}$ can be used as an additive for animal feed or as a pharmaceutical or dietary supplement for human consumption.

The yeast according to the invention may be of the genus *Kluyveromyces* (e.g. *K. lactis*; *K. marxianus*), preferably *K. lactis*, and/or of the genus *Yarrowia*, preferably *Y. lipolytica*. However, the strain may also be of the genus *Debaryomyces* (e.g. *Debaryomyces hansenii*), *Candida* (e.g. *Candida versatilis*), *Cryptococcus*, *Rhodotorula*, *Pichia*, *Trichosporon* (e.g. *Trichosporon beigelii*), *Torulaspora*, *Issatchenkia* (e.g. *Issatchenkia orientalis*), *Geotrichum*, *Saccharomyces* or *Zygosaccharomyces*. Such cells are available in the art and can be either obtained from deposit institutions or they can be isolated from food products.

EXAMPLES

Example 1—Preparation of *Propionibacterium*-Tolerant Yeast Cells

The yeast *Candida utilis* NRRL Y-7586 was cultivated in YEPD medium consisting of yeast extract (20 g/L), peptone (20 g/L) and dextrose (10 g/L) at 35° C. for 72 hours, washed twice with 0.1 M phosphate buffer (pH 7) and exposed to an adequate dose of an mutagenic agent (ethyl methanesulfonate) to obtain a 99.9% kill rate. Any other suitable fungal cell or yeast cell can be used. The surviving cells were cultivated in a medium containing yeast extract (10 g/L) and acetic and propionic acid at the minimal inhibitory concentration. After three days of cultivation at 35° C. an aliquot from this broth was transferred to YEPD medium, left to grow for 72 hours and subjected to another round of mutagenesis. The surviving cells are then cultivated in a medium containing yeast extract (10 g/L) and an increased concentration of acetic and propionic acid (relative to the previous round). This procedure was iteratively repeated until the yeast was able to tolerate high concentrations of acetic and propionic acids (i.e. yeast able to grow and consume acetic and propionic acid in concentrations of 15 g/L). In this way the strain *C. utilis* ABLMCU1 was obtained.

With the resulting *C. utilis* strain (ABLMCU1), which was tolerant to high concentrations of acetic and propionic acids, a similar mutagenesis/selection scheme was used, this time using diluted stationary-phase supernatant from fermentation of *propionibacterium* as the inhibitory agent. In more detail, *C. utilis* cells, previously selected to be tolerant to organic acids, were grown in YEPD medium, subjected to ethyl methanesulfonate and subsequently cultivated on a medium which was a mixture of the stationary-phase supernatant obtained from fermentation of *Propionibacterium freudenreichii* strain ABLM1700 in whey (whey, 5 g/L yeast extract, 20 mg/L $CoCl_2$, *Propionibacterium freudenreichii* cultivated for 96 hours at 35° C., supernatant hereinafter referred to as medium "As") and the medium used for the development of yeast cells tolerant to organic acids (i.e. acetic acid (15 g/L), propionic acid (15 g/L) and yeast extract (10 g/L) (herein referred to as medium "Bs"). These media were mixed in a ratio of As:Bs=3:7, which was above the level where ABLMCU1 yeast cells were able to grow. After 72 hours an aliquot of the resulting *C. utilis* culture was transferred to YEPD, grown and again exposed to ethyl methanesulfonate and subsequently transferred to the mixture of the media As and Bs at a higher ratio of As:Bs, namely 4:6. This procedure was repeated until yeast colonies were obtained, which were tolerant to undiluted stationary-phase supernatant of a fermentation of *propionibacterium* (100% As). The resulting yeast strain was deposited on 14 Jan. 2014 at the Deutsche Sammlung von Mikroorganismen und Zellkulturen (DSMZ) and is available under accession number DSM 28271.

The procedure described above resulted in a *propionibacterium*-tolerant *C. utilis* strain. It should be noted, however, that a similar procedure was used successfully to produce other *propionibacterium*-tolerant strains, i.e., starting from a different yeast strain. For example, *Kluyveromyces lactis* Y-17597 strain was treated in a similar procedure and resulted in *propionibacterium*-tolerant fungal strains (*K. lactis* ABLMKL6) according to the invention. The procedure was hence shown to be reproducible and applicable to other yeast strains.

Example 2—Test for Establishing the "Ability to Grow in a Stationary Phase Supernatant of a *Propionibacterium* Cultivation"

The following method is useful for determining whether a fungal stain, e.g. a yeast strain, is "capable of growing in a stationary-phase supernatant of a *propionibacterium* cultivation", according to claim 1.

Step 1: Obtaining a Stationary-Phase Supernatant of a *Propionibacterium* Cultivation A first-stage *propionibacterium* seed culture is prepared in medium P1 (Table 1, below) as follows. 100 μL of *propionibacterium* stock culture, obtained from the culture collection (*Propionibacterium freudenreichii* ATCC 6207) is transferred to 50 mL of medium P1 and incubated for 4 days at 35° C. without aeration and without shaking.

15 mL of this first-stage seed culture is then transferred to a 150 mL glass bottle filled with 135 mL of medium P2 (Table 2, below) and incubated for 4 days at 35° C. without aeration and without shaking to obtain a second-stage seed culture.

100 mL of the so obtained second-stage seed culture is then used to inoculate a 1 L working volume stirred tank bioreactor filled with 900 mL of medium P3 (Table 3, below). The cultivation parameters are: temperature: 35±0.5° C., pH: 6.5±0.1 (controlled with 15% NaOH or $H_2SO_4$), agitation: 100±10 RPM, sparging with $CO_2$: 0.1±0.05 vvm, $NH_4^+$ concentration: 400±100 mg/L (adjusted every 12 hours using 15% $(NH_4)_2SO_4$, pH 6.5). The fermentation is run until the concentration of lactose is below 1 g/L. At the end of the fermentation, the sum of the concentrations of acetic acid and propionic acid in the broth is preferably greater or equal to 20 g/L.

50 mL of the fermentation broth so obtained is centrifuged at 10000 g and the supernatant is transferred to an Erlenmeyer flask and autoclaved at 121° C. for 20 minutes. The autoclaved medium is a "stationary-phase supernatant of a *propionibacterium* cultivation".

Step 2: Testing the Ability to Grow in Stationary Phase Supernatant of a *Propionibacterium*

An inoculum of the fungal cell to be tested is prepared by adding 100 μL of a stock culture to 10 mL of Y1 medium (Table 4). The inoculum culture is incubated on a rotary shaker at 35° C. and 200 RPM for 72 hours. The resulting culture is used as the "fungal inoculum" in the following steps.

The autoclaved Erlenmeyer flask containing the stationary-phase supernatant obtained in Step 1 above is inoculated with 2.5 mL of the fungal inoculum and incubated on a rotary shaker at 35° C. and 200 RPM. The initial pH value is set to pH 6.5. This is considered the "test cultivation".

Growth of the fungus is evaluated by measuring changes in the pH of the culture after 24 hours of cultivation. In one embodiment, a tested fungal cell is considered to be "capable of growing in a stationary-phase supernatant of a *propionibacterium*", within the meaning of the appended claim 1, if the pH value of the broth in the test cultivation increases from the starting pH (pH 6.5) to a pH value of 8.0 or higher after 24 h of cultivation time.

Accordingly, the tested fungal cell may be regarded as not being capable of growing in a stationary-phase supernatant of a *propionibacterium* cultivation, if the pH value of the broth in the test cultivation remains below 8.0 after 24 h of cultivation time.

The claimed fungal cell being capable of growing in a stationary-phase supernatant of a *propionibacterium* cultivation is preferably one testing positive in the above test.

Example 2b—Alternative Tests

Alternatively, growth of the fungus can be evaluated by measuring changes OD of the culture after 24 hours of cultivation.

A tested fungal cell may be regarded as capable of growing in a stationary-phase supernatant of a *propionibacterium* cultivation, within the meaning of the appended claim 1, if the difference of the optical density (measured at 620 nm) of the broth is increased by at least 0.5 within 24 h after inoculation. Alternatively, a tested fungal cell is regarded as capable of growing in a stationary-phase supernatant of a *propionibacterium* cultivation, within the meaning of the appended claim 1, if the maximum growth rate ($\mu_{max}$) of the fungal cell in the test cultivation is equal to 0.02 $h^{-1}$ or above.

Accordingly, a tested fungal cell is regarded as not being capable of growing in a stationary-phase supernatant of a *propionibacterium* cultivation, within the meaning of the appended claim 1, if the difference of the optical density (measured at 620 nm) of the broth is increased by less than 0.5 within 24 h after inoculation. Alternatively, a tested fungal cell is regarded as not being capable of growing in a stationary-phase supernatant of a *propionibacterium* cultivation, within the meaning of the appended claim 1, if the maximum growth rate ($\mu_{max}$) of the fungal cell in the test cultivation below 0.02 $h^{-1}$.

Accordingly, the claimed fungal cell being capable of growing in a stationary-phase supernatant of a *propionibacterium* cultivation is one testing positive in one of the above alternative tests.

TABLE 1

Defined medium P1 for propionibacterium

| Ingredient | Amount |
|---|---|
| Trypticase (BBL) | 10 g |
| Yeast extract (Difco) | 10 g |
| Sodium DL-lactate (Sigma) | 10 g |
| $KH_2PO_4$ (Sigma) | 2.5 g |
| $MnSO_4$ (Sigma) | 0.05 g |
| Distilled water | up to 1000 mL | pH is adjusted to 7.0 with NaOH/HCl
autoclave for 20 minutes at 121° C. @ 1.2 bar

TABLE 2

Defined medium P2 for propionibacterium

| Ingredient | Amount |
|---|---|
| Glucose (Sigma) | 40 g |
| Sodium DL-lactate (Sigma) | 40 g |
| Yeast extract (Biolife) | 10 g |
| $CaCO_3$ (Sigma) | 10 g |
| $CoCl_2$ (Sigma) | 10 mg |
| Calcium D-panthotenate* (Sigma) | 20 mg |
| Distilled water | up to 1000 mL | pH is adjusted to 7.0 with NaOH/HCl
autoclave for 20 minutes at 121° C. @ 1.2 bar
*Added after sterilization

TABLE 3

Medium P3 for propionibacterium

| Ingredient | Amount |
|---|---|
| Sweet whey powder** | 60 g/L |
| Yeast extract (Biolife) | 5 g/L |
| Calcium D-panthotenate* (Sigma) | 40 mg/L | autoclave for 20 minutes at 121° C. @ 1.2 bar
*Added after sterilization
**Food-grade sweet whey powder with the following specifications: lactose min. 63% wt., protein min. 10% wt., moisture max. 5% is suitable and can be obtained from different suppliers such as: Hoogwegt International (Netherlands), Lactalis Ingredients (France), James Farrell & Co (USA).

TABLE 4

Medium Y1 for yeast

| Ingredient | Amount |
|---|---|
| Bacto peptone (Biolife) | 20 g |
| Yeast extract (Biolife) | 10 g |
| Glucose (Sigma) | 20 g |
| Distilled water | up to 1000 mL | autoclave for 20 minutes at 121° C. @ 1.2 bar

Example 3—Effective Co-Cultivation of *Propionibacterium* and Yeast i) *Propionibacterium* Inoculum Preparation The inoculum of *propionibacterium* was prepared in two stages. A 0.5 mL stock suspension of *Propionibacterium freudenreichii* ABLM2475 (any other vitamin B12-producing strain, such as *Propionibacterium freudenreichii* ATCC6207, could have been used) was inoculated into 50 mL of the first vegetative medium (yeast extract 20 g/L and DL-lactate 20 g/L) and incubated for 4 days at 35° C. The first vegetative stage was then transferred to 400 mL of the second-stage vegetative medium (glucose 40 g/L, yeast extract 40 g/L, DL-lactate 40 g/L, calcium carbonate 10 g/L, cobalt chloride 20 mg/L, pantothenate 10 mg/L) and cultivated for 4 days while pH value being continuously neutralised with sodium hydroxide. The entire second stage was then transferred to the final bioreactor.

ii) Tolerant Yeast Inoculum Preparation

The inoculum of tolerant yeast was also prepared in two stages. A 0.5 mL stock suspension of the yeast DSM 28271 was inoculated into 50 mL of the first vegetative medium (yeast extract 40 g/L, peptone 40 g/L and glucose 10 g/L) in a 250 mL Erlenmeyer flask and incubated for 2 days at 35° C. on a rotary shaker at 220 RPM. The first vegetative stage was then transferred into 200 mL of the same medium in a 1000 mL Erlenmeyer flask and cultivated for 2 days at 35° C. on a rotary shaker at 220 RPM.

iii) Fermentation

A 7 L working volume bioreactor was filled with 4 L of sour whey (COD was 80,000 mg $O_2$/L) supplemented with yeast extract (5 g/L) and cobalt chloride (20 mg/L) and sterilized for 1 hour at 121° C. After cooling to 35° C. pantothenate (10 mg/L) was added and the bioreactor inoculated with seed culture of *propionibacterium*. The cultivation temperature was 35° C. and the agitation rate 100 RPM. The content of the bioreactor was sparged with $CO_2$ gas (10 mL/min) and the pH was maintained at 6.5 (with NaOH). After 90 hours the lactate and lactose have been exhausted and approximately 8 and 15 g/L acetic and propionic acid were produced. At this time 20 mg/L 5,6-dimethylbenzimidazole was added, the agitation rate was increased to 500 RPM and aeration introduced at 1 vvm and the bioreactor was inoculated with 5% of the tolerant yeast. The pH value was maintained at 6.5 (with $H_2SO_4$). After 48 hours all the organic acids were consumed by yeast and the fermentation was stopped. The process yielded 15 mg/L of vitamin B12. The biomass consisting of *propionibacterium* and yeast was removed by centrifugation and the COD value of the resulting supernatant was 12,000 mg $O_2$/L, a 85% reduction.

Figure 3:
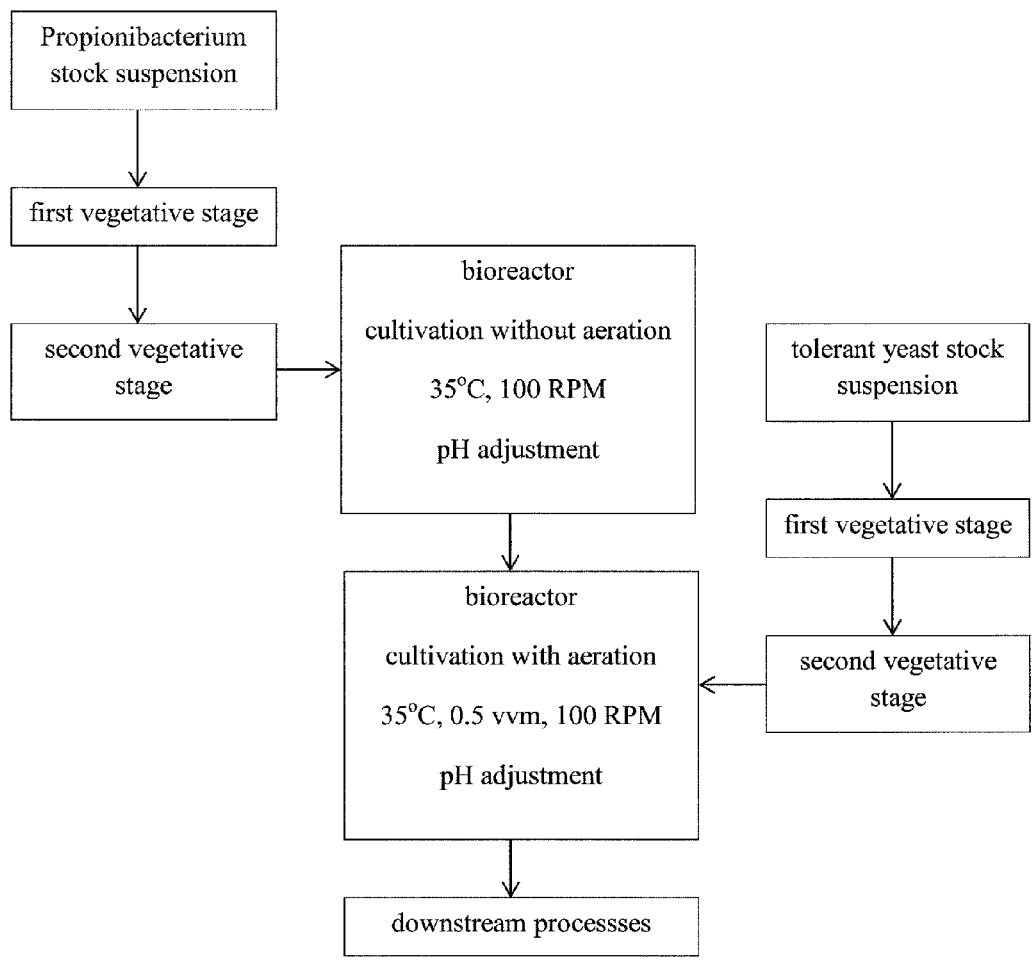
FIG. 3 shows a schematic presentation of a bioprocess for the co-cultivation of *Propionibacterium* sp. with tolerant yeast, according to the invention.
Figure 4:
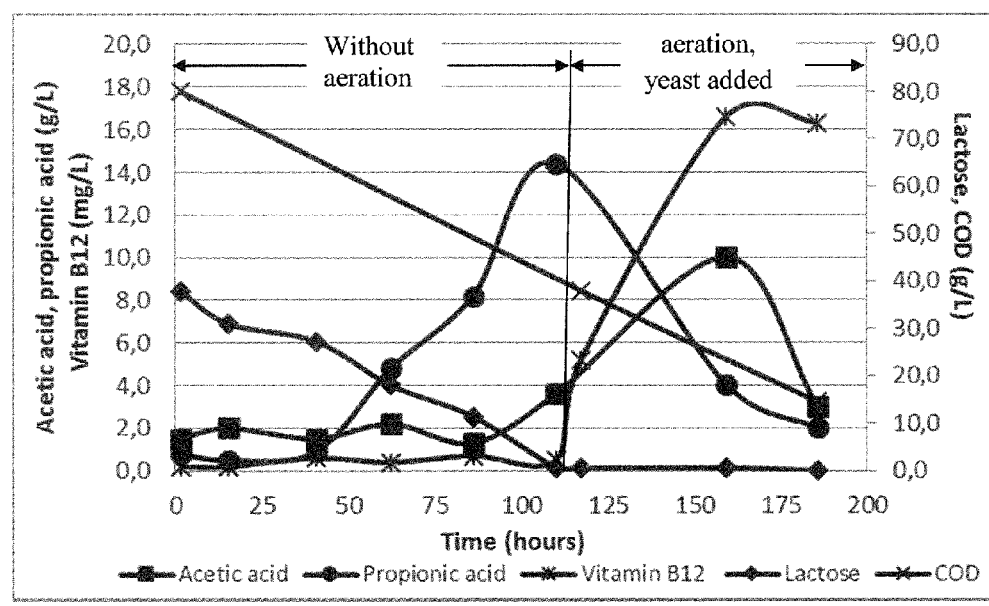
FIG. 4 shows the utilization of lactose by *Propionibacterium* sp. and the production of acetic and propionic acid and vitamin B12 in a two stage process on whey where tolerant *K. lactis* ABLMKL6 yeast culture was added in the stage where oxygen was introduced. In this way the COD value can be reduced from 80000 mg $O_2$/L to 14500 mg $O_2$/L. Up to 112 hours the fermentation was carried out without aeration and after 112 hours yeast and aeration was introduced.

A schematic flow sheet of the exemplary process is shown in FIG. 3.

Example 4—Effective Co-Cultivation of *Propionibacterium* and Yeast (*K. lactic* ABLMKL6)

i) *Propionibacterium* Inoculum Preparation

The inoculum of *propionibacterium* was prepared in two stages. A 0.5 mL stock suspension of *Propionibacterium freudenreichii* ABLM2475 (any other vitamin B12-producing strain, such as *Propionibacterium freudenreichii* ATCC6207, could have been used) was inoculated into 50 mL of the first vegetative medium (yeast extract 20 g/L and DL-lactate 20 g/L) and incubated for 4 days at 35° C. The first vegetative stage was then transferred to 400 mL of the second-stage vegetative medium (glucose 40 g/L, yeast extract 40 g/L, DL-lactate 40 g/L, calcium carbonate 10 g/L, cobalt chloride 20 mg/L, pantothenate 10 mg/L) and cultivated for 4 days while pH value being continuously neutralised with sodium hydroxide. The entire second stage was then transferred to the final bioreactor.

ii) Tolerant Yeast Inoculum Preparation

The inoculum of tolerant yeast was also prepared in two stages. A 0.5 mL stock suspension of the tolerant yeast *K.*

*lactic* ABLMKL6 was inoculated into 50 mL of the first vegetative medium (yeast extract 40 g/L, peptone 40 g/L and glucose 10 g/L) in a 250 mL Erlenmeyer flask and incubated for 2 days at 35° C. on a rotary shaker at 220 RPM. The first vegetative stage was then transferred into 200 mL of the same medium in a 1000 mL Erlenmeyer flask and cultivated for 2 days at 35° C. on a rotary shaker at 220 RPM.

iii) Fermentation

A 7 L working volume bioreactor was filled with 4 L of sour whey (COD was 80,000 mg $O_2$/L) supplemented with yeast extract (5 g/L) and cobalt chloride (20 mg/L) and sterilized for 1 hour at 121° C. After cooling to 35° C. pantothenate (10 mg/L) was added and the bioreactor inoculated with seed culture of *propionibacterium*. The cultivation temperature was 35° C. and the agitation rate 100 RPM. The content of the bioreactor was sparged with $CO_2$ gas (10 mL/min) and the pH was maintained at 6.5 (with NaOH). After 112 hours the lactate and lactose have been exhausted and approximately 4 and 14 g/L acetic and propionic acid were produced. At this time 20 mg/L 5,6-dimethylbenzimidazole was added, the agitation rate was increased to 500 RPM and aeration introduced at 1 vvm and the bioreactor was inoculated with 5% of the tolerant yeast. The pH value was maintained at 6.5 (with $H_2SO_4$). After 72 hours all the organic acids were consumed by yeast and the fermentation was stopped. The process yielded 16 mg/L of vitamin B12. The biomass consisting of *propionibacterium* and yeast was removed by centrifugation and the COD value of the resulting supernatant was 14,500 mg $O_2$/L, a 81% reduction.

The invention claimed is:

1. A yeast cell deposited on 14 Jan. 2014 at the Deutsche Sammlung von Mikroorganismen and Zellkulturen (DSMZ), Braunschweig, Germany, and available under accession number DSM 28271.

2. A fungal cell capable of growing in a stationary-phase supernatant of a *propionibacterium* cultivation at a maximum growth rate ($\mu_{max}$) of at least 0.02 $h^{-1}$ wherein said stationary-phase supernatant is obtained from a stationary culture of *Propionibacterium freudenreichii* cultivated without aeration at 35° C. in a liquid medium consisting of 60 g/L sweet whey powder, 5 g/L yeast extract, and 40 mg/L calcium D-pantothenate in water.

3. The fungal cell of claim 2, wherein the fungal cell is a yeast cell.

4. A process for producing a biotechnological product, said process comprising co-cultivation of *propionibacterium* and the fungal cell of claim 2 in a cultivation medium.

5. The process of claim 4, wherein said biotechnological product is produced by said *propionibacterium*.

6. The process of claim 4, wherein said biotechnological product is vitamin B12.

7. The process of claim 4, wherein said process includes a phase without aeration followed by an aerobic phase.

8. The process of claim 4, wherein at least 90% of the growth of the *propionibacterium* occurs during the phase without aeration.

9. The process of claim 4, wherein at least 90% of the growth of the fungal cell occurs during the aerobic phase.

10. The process of claim 4, wherein the chemical oxygen demand (COD) of the medium is reduced to a level of equal to or less than 25% of the initial COD of the cultivation medium.

11. The process of claim 4, wherein said cultivation medium comprises whey.

12. The process of claim 4, wherein the chemical oxygen demand (COD) of the medium is reduced to a level of equal to or less than 10% of the initial COD of the cultivation medium.

* * * * *